United States Patent
Sturla et al.

(12) 
(10) Patent No.: US 6,569,407 B1
(45) Date of Patent: May 27, 2003

(54) COMPOSITIONS CONTAINING A POLYCONDENSATE COMPRISING AT LEAST ONE POLYURETHANE AND/OR POLYUREA UNIT AND A SILICONE COMPRISING AT LEAST ONE CARBOXYLIC FUNCTION

(75) Inventors: Jean-Michel Sturla, Boulogne Billancourt (FR); Jean-Luc Bremenson, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/385,003

(22) Filed: Aug. 27, 1999

(30) Foreign Application Priority Data

Aug. 27, 1998 (FR) .............................. 98 10781

(51) Int. Cl.$^7$ .......................... A61K 7/06; A61K 7/11; A61K 31/695; A61K 7/09; A61L 9/14
(52) U.S. Cl. ........................ 424/47; 424/45; 424/401; 424/70.11; 424/70.12; 514/772.1; 514/770; 514/63; 222/631; 222/635
(58) Field of Search ................. 222/631, 635; 514/772.1, 63, 770; 424/70.11, 401, 45, 70.12, 47

(56) References Cited

U.S. PATENT DOCUMENTS

| | | | |
|---|---|---|---|
| 4,931,062 A | | 6/1990 | Bay et al. |
| 5,626,840 A | * | 5/1997 | Thomaides et al. ...... 424/79.11 |
| 5,643,581 A | | 7/1997 | Mougin et al. |
| 6,166,093 A | * | 12/2000 | Mougin et al. .......... 514/772.1 |

FOREIGN PATENT DOCUMENTS

| | | |
|---|---|---|
| DE | 42 25 045 | 2/1994 |
| DE | 42 41 118 | 6/1994 |
| DE | 43 38 849 | 5/1996 |
| DE | 195 41 326 | 5/1997 |
| EP | 0 542 072 | 5/1993 |
| EP | 0 582 152 | 2/1994 |
| EP | 0 619 111 | 10/1994 |
| EP | 0 636 361 | 2/1995 |
| EP | 0 637 600 | 2/1995 |
| EP | 0 648 485 | 4/1995 |
| EP | 0 656 021 | 6/1995 |
| EP | 0 745 373 | 12/1996 |
| EP | 0 751 162 | 1/1997 |
| EP | 0 756 860 | 2/1997 |
| EP | 0 779 310 | 6/1997 |
| EP | 0 838 211 | 4/1998 |
| EP | 0 838 212 | 4/1998 |
| FR | 2 743 297 | 7/1997 |
| FR | 2 749 568 | 12/1997 |
| WO | WO 93/23009 | 11/1993 |
| WO | WO 94/03510 | 2/1994 |
| WO | WO 96/14049 | 5/1996 |
| WO | WO 96/14050 | 5/1996 |
| WO | WO 97/15275 | 5/1997 |
| WO | WO 97/25021 | 7/1997 |
| WO | WO 98/20833 | 5/1998 |

OTHER PUBLICATIONS

English language Derwent Abstract of DE 44 38 489.
English language Derwent Abstract of DE 195 41 326.
English language Derwent Abstract of EP 0 636 631.
English language Derwent Abstract of EP 0 637 600.
English language Derwent Abstract of EP 0 648 485.
English language Derwent Abstract of EP 0 745 373.
English language Derwent Abstract of EP 0 751 162.
English language Derwent Abstract of EP 0 756 860.
English language Derwent Abstract of FR 2 743 297.
English language Derwent Abstract of FR 2 749 568.
Derwent Publications, Ltd., London, GB; AN 93–410762 (JP 05 310535).
English language Derwent Abstract of DE 42 41 118.
English language Derwent Abstract of DE 42 25 045.
English language abstract of EP 0 542 072.
English language Derwent Abstract of EP 0 656 021.
English language abstract of EP 0 779 310.

* cited by examiner

Primary Examiner—Frederick Krass
Assistant Examiner—Clinton Ostrup
(74) Attorney, Agent, or Firm—Finnegan, Henderson, Farabow, Garrett & Dunner, L.L.P.

(57) ABSTRACT

The invention relates to hair compositions comprising, in a cosmetically acceptable medium, a polycondensate comprising at least one polyurethane and/or polyurea unit and a silicone comprising at least one carboxylic function. The invention is also directed towards a process for shaping or maintaining the hairstyle, comprising the use of these compositions, and to their use for the manufacture of hair products, in order to maintain or shape the hairstyle.

2 Claims, No Drawings

COMPOSITIONS CONTAINING A POLYCONDENSATE COMPRISING AT LEAST ONE POLYURETHANE AND/OR POLYUREA UNIT AND A SILICONE COMPRISING AT LEAST ONE CARBOXYLIC FUNCTION

The invention relates to compositions, such as those for hair styling, comprising, in a cosmetically acceptable medium, a polycondensate, such as a multiblock polymer, comprising at least one polyurethane and/or polyurea unit and a silicone comprising at least one carboxylic functional group. The invention is also directed towards a process for shaping or maintaining a hairstyle comprising the use of these compositions, and to their use for the manufacture of hair products, in order to maintain or shape the hairstyle.

Fixing of the hairstyle is an important element of styling which comprises maintaining the shape already given or in shaping the hair and fixing it simultaneously.

Hair products for shaping and/or maintaining the hairstyle which are the most common on the cosmetics market are spray compositions comprising a solution, usually an alcoholic or aqueous solution, and one or more materials, generally polymer resins (also known as fixing materials), the function of which is to form welds between the hairs, as a mixture with various cosmetic adjuvants. This solution can be packaged, for example, in a suitable aerosol container placed under pressure using a propellant. The construction and operation of such aerosol containers is well known to those skilled in the art.

Compositions intended for fixing and/or maintaining the hairstyle sometimes have the drawback of adversely affecting the cosmetic properties of the hair. Thus, the hair can become coarse and lose its natural softness. Styling compositions are thus sought which fix and/or maintain the hairstyle well while at the same time afford good cosmetic properties.

Patent DE 195 41 326 discloses styling compositions distributed from an aerosol device, which contain, in an aqueous-alcoholic medium, a polymer containing polyurethane units as fixing polymer, and a propellant. These compositions, which are already satisfactory in terms of fixing of the hairstyle, can, however, be improved in particular as regards the cosmetic properties which they give to the hair.

The inventors have discovered that by combining certain silicones with a polycondensate containing at least one polyurethane and/or polyurea unit, it is possible to satisfy the requirements mentioned above.

The subject of the invention is thus a composition, such as a hair styling composition, comprising, in a cosmetically acceptable medium, in relative proportions by weight relative to the total weight of the composition, from 0.1 to 20%, inclusive, of a polycondensate comprising at least one sequence chosen from polyurethanes and polyureas, characterized in that it also comprises from 0.01 to 20%, inclusive, of at least one silicone chosen from partially and totally neutralized silicone compounds comprising at least one carboxylic functional group and salts thereof.

Another subject of the invention relates to a process for shaping or maintaining the hairstyle, comprising the use of this composition.

Yet another subject of the invention relates to the use of this composition for the manufacture of hair compositions, in order to maintain or fix the hairstyle.

Examples of polycondensates comprising at least one polyurethane and/or polyurea compound according to the present invention include, but are not limited to, those described in patents EP 0,751,162, EP 0,637,600, FR 2,743,297, and EP 0,648,485, all assigned to the present assignee, as well as patents EP 0,656,021 and WO 94/03510 from the company BASF, and EP 0,619,111 from the company National Starch. The disclosures of these documents are specifically incorporated herein by reference.

The polycondensates used in accordance with the invention can be soluble in a cosmetically acceptable medium, in particular after neutralization with an organic or inorganic base, or alternatively can form a dispersion in this medium. In the latter case, the dispersion can generally comprise at least 0.05% of surfactant, which allows the polycondensate to form a dispersion and to be maintained in dispersion.

According to the invention, any type of surfactant can be used in the dispersion, including a nonionic surfactant. In certain embodiments, the average size of the polycondensate particles in the dispersion is between 0.1 and 1 micron (micrometer), inclusive.

By way of example, the polycondensate can be formed by an arrangement of blocks, this arrangement being obtained in particular using:
(1) at least one compound which contains at least two active hydrogen atoms per molecule;
(2) at least one diol containing at least one functional group chosen from acid radicals and salts thereof; and
(3) at least one isocyanate chosen from di- and polyisocyanates. Compound (1) can be chosen from diols, diamines, polyesterols, polyetherols.

In certain embodiments, compound (1) can be a linear polyethylene and polypropylene glycol, in particular those which are obtained by reaction of ethylene oxide or propylene oxide with water or diethylene or dipropylene glycol in the presence of sodium hydroxide as catalyst. These polyglycols generally have a molecular weight ranging from about 600 to 20,000.

Other suitable organic compounds that can be used are those which have mercapto, amino, carboxyl, or hydroxyl groups. Among these, mention may be made more particularly of polyhydroxy compounds such as polyether diols, polyester diols, polyacetal diols, polyamide diols, polyesterpolyamide diols, poly(alkylene ether) diols, polythioether diols, and polycarbonate diols.

In certain embodiments, the polyether diols are the condensation products of ethylene oxide, of propylene oxide, or of tetrahydrofuran; their copolymerization or condensation products, which may be grafted or blocks, such as mixtures of condensates of ethylene oxide and propylene oxide; and the products of polymerization of olefins, at high pressure, with alkylene oxide condensates. Suitable polyethers are prepared, for example, by condensation of alkylene oxides and polyhydric alcohols, such as ethylene glycol, 1,2-propylene glycol, and 1,4-butanediol.

The polyester diols, polyesteramides, and polyamide diols can be saturated and can be obtained, for example, from the reaction of saturated or unsaturated polycarboxylic acids with polyhydric alcohols, diamines, or polyamines. Adipic acid, succinic acid, phthalic acid, terephthalic acid, and maleic acid can be used, for example, to prepare these compounds. Polyhydric alcohols that are suitable for preparing the polyesters include, but are not limited to, ethylene glycol, 1,2-propylene glycol, 1,4-butanediol, neopentyl glycol, and hexanediol. Amino alcohols, for example ethanolamine, can also be used. Diamines that are suitable for preparing the polyesteramides include ethylenediamine and hexamethylenediamine.

Suitable polyacetals can be prepared, for example, from 1,4-butanediol or from hexanediol, and from formaldehyde.

Suitable polythioethers can be prepared, for example, by condensation reaction between thioglycols, either alone or in combination with other glycols such as ethylene glycol, 1,2-propylene glycol or with other polyhydroxylated compounds. Polyhydroxylated compounds already containing urea or urethane groups and natural polyols, which can be further modified, for example castor oil and carbohydrates, can also be used.

In certain embodiments, compound (1) is a polyesterol, in particular a polyester diol formed by the reaction of at least one (di)polyol ($1_a$) and at least one acid ($1_b$). The (di)polyol ($1_a$) can be chosen from the group comprising neopentyl glycol, 1,4-butanediol, hexanediol, ethylene glycol, diethylene glycol, propylene glycol, butylene glycol, neopentyl glycol, and (di)polyethylene glycol. The acid ($1_b$) can be chosen from the group comprising phthalic acid, isophthalic acid, adipic acid, and (poly)lactic acid.

A hydroxycarboxylic acid such as dimethylol-propanoic acid (DMPA) or a 2,2-hydroxymethylcarboxylic acid can be used as compound (2). In general, compound (2) is useful as a coupling block. In certain embodiments, compound (2) comprises at least one poly(($\alpha$-hydroxydiolcarboxylic) acid). In certain other embodiments, compound (2) comprises 2,2-di(hydroxy-methyl)acetic acid, 2,2-dihydroxymethylpropionic acid, 2,2-dihydroxymethylbutyric acid, or 2,2-dihydroxymethylpentanoic acid.

The isocyanate compound (3) can be chosen from, but is not limited to, hexamethylene diisocyanate, isophorone diisocyanate (IPDI), toluylene diisocyanate, diphenylmethane 4,4'-diisocyanate (DPMD), dicyclohexylmethane 4,4'-diisocyanate (DCMD), methylenebis(p-phenyl) diisocyanate, methylenebis(4-cyclohexyl isocyanate), isophorone diisocyanate, toluene diisocyanate, 1,5-naphthalene diisocyanate, 4,4'-diphenylmethane diisocyanate, 2,2'-dimethyl-4,4'-diphenylmethane diisocyanate, 1,3-phenylene diisocyanate, 1,4-phenylene diisocyanate, mixtures of 2,4- and 2,6-toluene diisocyanate, 2,2'-dichloro-4,4'-diisocyanatodiphenylmethane, 2,4-dibromo-1,5-diisocyanatonaphthalene, butane 1,4-diisocyanate, 1,6-hexane diisocyanate, and 1,4-cyclohexane diisocyanate.

The polycondensate can be formed using at least one additional compound (4), which generally serves to extend the polycondensate chain. Examples of compounds suitable as compound (4) include, but are not limited to, saturated or unsaturated glycols such as ethylene glycol, diethylene glycol, neopentyl glycol, or triethylene glycol; amino alcohols such as ethanolamine, propanolamine or butanolamine; heterocyclic, aromatic, cycloaliphatic and aliphatic primary amines; diamines; carboxylic acids such as aliphatic, aromatic or heterocyclic carboxylic acids, for instance oxalic acid, succinic acid, glutaric acid, adipic acid, sebacic acid, or terephthalic acid; and amino carboxylic acids. In certain embodiments, compound (4) is an aliphatic diol.

The polycondensates in accordance with the invention can also be formed from at least one additional compound (5) having a silicone skeleton. In certain embodiments, compound (5) is chosen from polysiloxanes, polyalkylsiloxanes, and polyarylsiloxanes. In certain embodiments, compound (5) is a polyethylsiloxane, polymethylsiloxane, or a polyphenylsiloxane. For example, the polyalkylsiloxane can be chosen from polyethylsiloxanes or polymethylsiloxanes, and the polyarylsiloxane can be chosen from polyphenylsiloxanes. Compound (5) can optionally contain hydrocarbon-based chains grafted onto at least one silicon atom.

According to an embodiment of the compositions of the invention, the polyurethane and/or polyurea sequences of the polymer have a repeating base unit corresponding to the formula (I'):

—X'—B—X'—CO—NH—R—NH—CO— (I')

in which:

X' is chosen from O and NH,

B is a divalent hydrocarbon-based radical, this radical being substituted or unsubstituted, and R is a divalent substituted or unsubstituted radical chosen from aromatic alkylene radicals, $C_1$ to $C_{20}$ aliphatic radicals, and $C_1$ to $C_{20}$ cycloaliphatic radicals.

In certain embodiments, radical B is a $C_1$ to $C_{30}$ radical and bears a group containing one or more carboxylic functional groups and/or one or more sulphonic functional groups, the carboxylic and/or sulphonic functional groups being in free form or else partially or totally neutralized with an inorganic or organic base. In certain embodiments, radical B is a $C_1$ to $C_{30}$ divalent hydrocarbon-based radical.

The radical R is advantageously chosen from radicals corresponding to the following formulae:

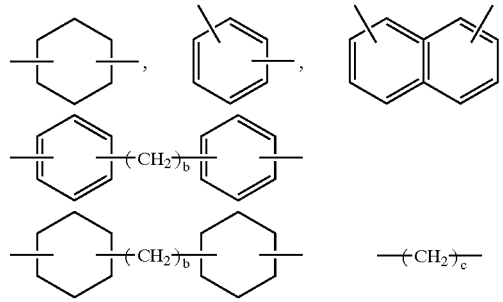

in which b is an integer between 0 and 3, inclusive, and c is an integer between 1 and 20, inclusive, such as between 2 and 12, inclusive.

In certain embodiments, radical R is chosen from hexamethylene, 4,4'-biphenylenemethane, 2,4- and/or 2,6-tolylene, 1,5-naphthylene, p-phenylene and methylene-4,4-bis-cyclohexyl radicals, and divalent radicals derived from isophorone.

The polycondensate used in accordance with the invention comprising at least one polyurethane and/or polyurea compound or unit can also comprise at least one polysiloxane compound in which the repeating base unit corresponds, for example, to the formula (II'):

—X'—P—X'—CO—NH—R—NH—CO— (II')

in which:

P is a polysiloxane segment,

X' is chosen from O and NH, and

R is chosen from divalent substituted and unsubstituted radicals chosen from aromatic alkylene radicals, $C_1$ to $C_{20}$ aliphatic radicals, and $C_1$ to $C_{20}$ cycloaliphatic radicals.

In certain embodiments, the polysiloxane segment P corresponds to the formula (III):

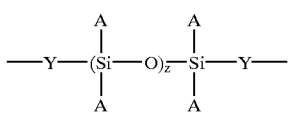

(III)

in which:
- the radicals A, which can be identical or different, are chosen from, on the one hand, $C_1$ to $C_{20}$ monovalent hydrocarbon-based radicals which are free or substantially free of ethylenic unsaturation and, on the other hand, aromatic radicals,
- Y represents a divalent hydrocarbon-based radical, and
- z represents an integer chosen such that the average molecular weight of the polysiloxane segment ranges from 300 to 10,000.

In general, the divalent radical Y is chosen from alkylene radicals of formula $-(CH_2)_a-$, in which a represents an integer which can range from 1 to 10, inclusive.

The radicals A can be, but are not necessarily, chosen from alkyl radicals, including methyl, ethyl, propyl, isopropyl, butyl, pentyl, hexyl, octyl, decyl, dodecyl and octadecyl radicals; cycloalkyl radicals, such as the cyclohexyl radical; aryl radicals, including phenyl and naphthyl; arylalkyl radicals, such as benzyl and phenylethyl; and tolyl and xylyl radicals.

The polycondensates used in accordance with the invention can be soluble in a cosmetically acceptable medium, in particular after neutralization with an organic or inorganic base, or else can form a dispersion in this medium. Generally, in the latter case, the dispersion comprises at least 0.05% surfactant, which allows the polycondensate to form a dispersion and to be maintained in dispersion.

According to the invention, any type of surfactant can be used in the dispersion, including a nonionic surfactant. The average size of the polycondensate particles in the dispersion is generally between 0.1 and 1 micron (micrometer), inclusive.

The composition in accordance with the invention generally comprises, in relative proportions by weight relative to the total weight of the composition, between 0.1 and 20%, inclusive, of the polycondensate comprising at least one sequence chosen from polyurethanes. In certain embodiments, the polycondensate comprises, on a weight-to-weight basis, between 1 and 15%, inclusive, of the composition. In certain embodiments, the polycondensate comprises between 2 and 8%, inclusive, by weight of the composition.

In certain embodiments, the silicones according to the present invention are those described in patent EP 0,756, 860, in patent application WO 98/20833, and in the French patent application whose application number is 97/16507, all assigned to the present assignee, and all of which are hereby incorporated by reference herein.

For the purposes of the present invention, the term silicone is understood to refer to any organosilicone polymer or oligomer of linear or cyclic, branched, or crosslinked structure, of variable molecular weight, obtained by polymerization and/or polycondensation of suitably functionalized silanes comprising a repetition of the main units in which silicon atoms are linked together by oxygen atoms to form a siloxane bond ($\equiv Si-O-Si\equiv$), with hydrocarbon-based radicals, which are optionally substituted, being directly linked from a carbon atom to the said silicon atoms. The most common hydrocarbon-based radicals are the alkyl radicals, especially $C_1-C_{10}$ alkyl radicals and in particular methyl, fluoroalkyl radicals, and aryl radicals and in particular phenyl.

According to a first embodiment of the compositions in accordance with the invention, the silicone comprising at least one carboxylic functional group is an organopolysiloxane comprising at least one unit corresponding to formula (I):

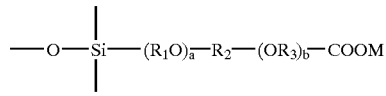

(I)

in which:
- $R_1$ and $R_3$ independently are chosen from linear and branched alkylene radicals having from 2 to 20 carbon atoms;
- $R_2$ is chosen from linear and branched alkylene radicals having from 1 to 50 carbon atoms and optionally comprising a hydroxyl group;
- a represents 0 or 1;
- b is a number ranging from 0 to 200; and
- M is chosen from hydrogen, alkali metals and alkaline-earth metals, $NH_4$, and quaternary ammonium groups such as, in particular, mono-, di-, tri- and tetra($C_1-C_4$ alkyl)- ammonium groups.

It is possible, for example, to use organopolysiloxanes containing carboxylic functions, corresponding to formula (II):

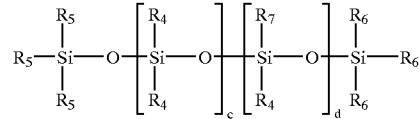

(II)

in which:
- the radicals $R_4$ are identical or different and are chosen from the group comprising linear and branched $C_1-C_{22}$ alkyl radicals, $C_1-C_{22}$ alkoxy radicals, and phenyl radicals,
- the radicals $R_5$, $R_6$, and $R_7$ are identical or different and are chosen from the group comprising linear and branched $C_1-C_{22}$ alkyl radicals, $C_1-C_{22}$ alkoxy radicals, phenyl-based radicals, and radicals $(R_1O)_a-R_2-(OR_3)_b-COOM$, with the restriction that at least one of the radicals $R_5$, $R_6$ or $R_7$ is a radical $-(R_1O)_a-R_2-(OR_3)_b-COOM$,
- the radicals $R_1$, $R_2$, $R_3$, a, b, and M have the same meanings as in formula (I),
- c and d are numbers ranging from 0 to 1000. In certain embodiments, the sum c+d ranges from 2 to 1000.

Among the silicones of formula (II), certain compounds are those which satisfy formula (III):

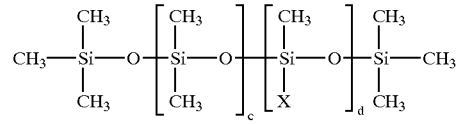

(III)

in which X is a radical $-(R_1O)_a-R_2-(OR_3)_b-COOM$, the radicals $R_1$, $R_2$, $R_3$, a, b, d, and M having the same meanings as for formulae (I) and (II).

As compounds corresponding to formula (III), it is possible, for example, to use those sold under the trade name Oil M 642, SLM 23 000/1 or SLM 23 000/2 by the company Wacker, or alternatively under the trade name 176-12057 by the company General Electric, or alternatively under the trade name FZ 3703 by the company OSI, or alternatively under the trade name BY 16 880 by the company Toray Silicone.

According to a second embodiment of the compositions in accordance with the invention, the silicone can be formed by a main silicone chain corresponding to the formula ($\equiv$Si—O—)$_n$ onto which is grafted, inside the chain as well as, optionally, on at least one of its ends, at least one hydrocarbon-based group comprising at least one carboxylic functional group.

The nature and/or amount of the hydrocarbon-based groups comprising at least one carboxylic functional group are chosen such that the corresponding silicone derivative is water-soluble or water-dispersible, after optional neutralization of the groups of anionic nature using an alkaline agent.

These specific silicone derivatives can be existing commercial products or alternatively can be obtained according to any means known to those skilled in the art, in particular by reaction between (i) a starting silicone which is correctly functionalized on one or more of these silicon atoms, and (ii) an anionic compound which is itself correctly functionalized with a functional group which is capable of reacting with the functional group(s) borne by the silicone, to form a covalent bond. A standard example of such a reaction is the hydrosilylation reaction between $\equiv$Si—H groups and vinylic groups CH$_2$=CH—, or alternatively the reaction between thio functional groups —SH with these same vinylic groups.

Examples of silicone derivatives comprising a main silicone chain on which is grafted, inside the said chain as well as, optionally, on its ends, at least one hydrocarbon-based group comprising at least one carboxylic functional group, which are suitable for carrying out the present invention, along with their specific mode of preparation, are described in particular in patent applications EP 0,582,152 and WO 93/23009, the disclosures of which are specifically incorporated herein by reference.

Silicone derivatives suitable for carrying out the present invention include those whose structure contains the following unit:

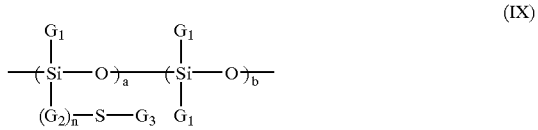

(IX)

in which G$_1$ is chosen from hydrogen, C$_1$–C$_{10}$ alkyl radicals, and phenyl radicals; G$_2$ is chosen from C$_1$–C$_{10}$ alkylene groups; G$_3$ is chosen from anionic polymer residues resulting from the (homo)polymerization of at least one anionic monomer containing ethylenic unsaturation; n is equal to 0 or 1; a is an integer which is between 1 and 50, inclusive; and b is an integer which is between 10 and 350, inclusive.

In certain embodiments, the unit of formula (IX) above has at least one of the following characteristics:
 G$_1$ is an alkyl radical, such as a methyl radical,
 n is non-zero, and G$_2$ represents a C$_1$–C$_3$ divalent radical, such as a propylene radical,
 G$_3$ represents a polymer radical resulting from the (homo)polymerization of at least one monomer of unsaturated carboxylic acid type, such as acrylic acid and/or methacrylic acid.

In certain embodiments, the unit of formula (IX) above has all of the above characteristics.

In certain embodiments, the amount of carboxylate groups in the final polymer is between 1 mol of carboxylate per 200 g of polymer and 1 mol of carboxylate per 5000 g of polymer, inclusive. In certain embodiments, the number-average molecular mass of the silicone polymer is between approximately 10,000 and approximately 1,000,000. In certain embodiments, the number-average molecular mass of the silicone polymer is between approximately 10,000 and 100,000.

Examples of silicone derivatives suitable for carrying out the present invention are, for example, those sold by the 3M company under the trade name Silicone "plus" Polymer VS 80. These products correspond to polydimethylsiloxanes (PDMSs) onto which are grafted, via a connecting chain of thiopropylene type, mixed polymer units of poly(meth)acrylic acid type and of polybutyl (meth)acrylate ester type. These products can be obtained conventionally by radical copolymerization between, on the one hand, a silicone of polydimethylsiloxane type prefunctionalized with thiopropyl groups, and, on the other hand, a monomer mixture consisting of (meth)acrylic acid and butyl (meth)acrylate.

Other silicones suitable for carrying out the present invention are silicones comprising at least one substituent containing at least two groups, which may be identical or different, chosen from carboxylic acids and salts thereof, amides, and esters, at least one of these groups being chosen from carboxylic acids and salts thereof.

In certain embodiments, these silicones comprise at least one unit of formula (IV):

(IV)

in which Z is a radical corresponding to formula (V) below:

(V)

in which:
 W, R$_2$, and R$_4$, which may be identical or different, are chosen from a covalent bond and linear and branched alkylene radicals having from 1 to 6 carbon atoms which can comprise a hydroxyl group,
 R$_3$ is chosen from a hydrogen atom and linear and branched C$_1$–C$_6$ alkyl radicals,
 X and X', which may be identical or different, are chosen from the radicals OM, NR$_5$R$_6$, and OR$_7$,
 M is chosen from a hydrogen atom; alkali metals (for example Na$^+$, K$^+$); NH$_4^+$; ammonium groups containing a residue from the group comprising basic amino acids such as lysine, arginine, sarcosine, ornithine and citrulline; and amino alcohols such as monoethanolamine, diethanolamine, triethanolamine, glucamine, N-methylglucamine, and 3-amino-1,2-propanediol,
 R$_5$ and R$_6$, which may be identical or different, are chosen from the group comprising hydrogen and linear and branched C$_1$–C$_6$ alkyls, or alternatively R$_5$ and R6 can together form a 5- or 6-membered heterocycle,
 R$_7$ is chosen from linear and branched C$_1$–C$_{30}$ alkyl radicals, and
 at least one of the groups X and X' denotes OM.

In formula (IV), the radicals R, which may be identical or different, are chosen from alkyl radicals, especially C$_1$–C$_{10}$ alkyl radicals and in particular methyl, fluoroalkyl radicals, especially $C_1$–$C_{10}$ fluoroalkyl radicals, $C_6$–$C_{12}$ aryl radicals and in particular phenyl. In certain embodiments, a is chosen from 0, 1 and 2. In certain embodiments, a is 1 or 2. In certain embodiments, the radicals R of formula (IV) are chosen from $C_1$ to $C_{10}$ alkyl radicals, $C_1$ to $C_{10}$ fluoroalkyl radicals, and $C_6$ to $C_{12}$ aryl radicals.

In certain embodiments, the silicones used comprise at least one unit of formula (IV), which satisfy at least one of the following conditions:

W denotes a covalent bond, $R_3$ denotes a hydrogen atom,

R denotes a methyl radical,

X and X' are chosen from OM and $NR_5R_6$, $R_2$ and $R_4$, which may be identical or different, are chosen from a covalent bond and a methyl radical. In certain embodiments, the silicones satisfy all of the above conditions.

The other units of the silicone can be chosen from those of formula (VI):

$$R_b SiO_{(4-b)/2} \qquad (VI)$$

in which R has the same meaning as in formula (IV) and b is equal to 0, 1, 2, or 3. In certain embodiments, b is equal to 2 or 3.

The silicones comprising at least one unit of formula (IV) are described in particular in U.S. Pat. No. 4,931,062, the disclosure of which is specifically incorporated herein by reference. Such silicones are sold, for example, under the trade name SLM 23 105 by the company Wacker and under the trade name Densodrin OF by the company BASF.

The relative proportion by weight, relative to the total weight of the composition, of silicone or of silicone mixture is generally between 0.01 and 20%, inclusive. In certain embodiments, the relative proportion is between 0.01 and 10%, inclusive. In certain embodiments, the relative proportion is between 0.05 and 5%, inclusive.

The composition in accordance with the invention can be, but does not have to be, in the form of a lotion or a gel. It can be applied, for example, by spraying, such as from a pump-dispenser bottle or an aerosol.

The packaging in aerosol form is especially practical for the user, who obtains fairly homogeneous distribution of the product without difficulty. However, this type of packaging can have the drawback of giving rise to a release of volatile organic compounds (VOCs) that are harmful to the environment. They originate in particular from the amount of organic solvent used and of propellant gas chosen to manufacture the composition. Thus, the preparation of cosmetic compositions packaged in aerosol form for which the amount of volatile organic compounds expelled is low, is included within the invention and is well within the ordinary skill in the art.

The quality of the spraying obtained by means of an aerosol device, i.e., essentially the distribution of the droplets in space at the nozzle outlet, can depend greatly on the chemical constitution of the composition used. It is desired to formulate cosmetic compositions which give rise to an optimum quality of spraying.

Generally, between 7.5 and 70%, inclusive, of the total weight of the composition is comprised of an organic solvent. In certain embodiments, between 10 and 50%, inclusive, of the total weight of the composition is comprised of an organic solvent. In certain embodiments, between 10 and 25%, inclusive, of the total weight of the composition is comprised of an organic solvent.

In accordance with the invention, the organic solvent can be chosen in particular from the group comprising $C_1$–$C_4$ lower alcohols such as ethanol, isopropanol; acetone; methyl ethyl ketone; methyl acetate; butyl acetate; ethyl acetate; dimethoxyethane; diethoxyethane; and mixtures thereof. In certain embodiments, ethanol is used.

The composition of the invention generally comprises, in relative proportions by weight relative to the total weight of the composition, between 15 and 85%, inclusive, of a propellant gas. In certain embodiments, the composition comprises between 25 and 60%, inclusive, on a weight-to-weight basis, of a propellant gas. In certain embodiments, the composition comprises between 30 and 50%, inclusive, on a weight-to-weight basis, of a propellant gas.

In accordance with the invention, a gas which is soluble or insoluble in the composition, such as dimethyl ether, fluoro or non-fluoro hydrocarbons, the usual liquefied gases used in body-treating compositions, or a mixture of these propellant gases can be used as propellant gas. In certain embodiments, dimethyl ether is used.

The concentrations and the nature of the various components can be chosen so as to reduce the contents of volatile organic compounds (VOCs).

The compositions in accordance with the invention can moreover contain at least one cosmetic additive. Examples of such additives include, but are not limited to, fatty substances, thickeners, softeners, anti-foaming agents, moisturizers, antiperspirants, basifying agents, dyes, pigments, fragrances, preserving agents, surfactants, hydrocarbon-based polymers, additional volatile and non-volatile silicones other than those described above, proteins, and vitamins.

In particular, it may be advantageous to add fixing polymers to the composition, such as nonionic, anionic, cationic, or amphoteric fixing polymers.

A better understanding of the invention may be gained with the aid of the non-limiting example which follows and which constitutes an advantageous embodiment of the compositions in accordance with the invention.

EXAMPLE

The composition below, for which the percentages are relative percentages by weight, is prepared.

| | |
|---|---|
| Lactic acid/ethylene glycol P(MIS-EG)-dimethylolpropanoic acid (DMPA)-isophorone-diisocyanate polyester polycondensate | 4% |
| Silicone "Plus" Polymer VS 80 | 0.2% |
| Aminomethylpropanol | qs neutralization |
| Ethanol | 15% |
| Dimethyl ether | 35% |
| Demineralized water | qs 100% |

What is claimed is:

1. A composition comprising:

a) Lactic acid/ethylene glycol P(MIS-EG)-dimethylolpropanoic acid (DMPA)-isophorone-diisocyanate polyester polycondensate;

b) a polydimethylsiloxane onto which is grafted, via a thiopropylene connecting chain, mixed polymer units of poly(meth)acrylic acid and polybutyl (meth)acrylate ester;

c) Aminomethylpropanol;
d) Ethanol;
e) Dimethyl ether; and
f) Demineralized water.

2. The composition according to claim 1, comprising:

a) 4%, by weight, lactic acid/ethylene glycol P(MIS-EG)-dimethylolpropanoic acid (DMPA)-isophorone-diisocyanate polyester polycondensate;

b) 0.2%, by weight, polydimethylsiloxane onto which is grafted, via a thiopropylene connecting chain, mixed polymer units of poly(meth)acrylic acid and polybutyl (meth)acrylate ester;

c) a sufficient amount of aminomethylpropanol to adjust the composition to a neutral pH;

d) 15%, by weight, ethanol;

e) 35%, by weight, dimethyl ether; and f) a sufficient amount of demineralized water to adjust the total weight to 100%.

* * * * *